United States Patent [19]

Schirmer et al.

[11] Patent Number: 4,642,132
[45] Date of Patent: Feb. 10, 1987

[54] AMINOTHIADIAZOLES AND THEIR USE FOR CONTROLLING UNDESIRABLE PLANT GROWTH

[75] Inventors: Ulrich Schirmer, Heidelberg; Peter Plath, Ludwigshafen; Hubert Sauter, Mannheim; Bruno Wuerzer, Otterstadt, all of Fed. Rep. of Germany

[73] Assignee: BASF Aktiengesellschaft, Ludwigshafen, Fed. Rep. of Germany

[21] Appl. No.: 685,211

[22] Filed: Dec. 26, 1984

Related U.S. Application Data

[63] Continuation of Ser. No. 457,179, Jan. 11, 1983, abandoned.

[30] Foreign Application Priority Data

Jan. 22, 1982 [DE] Fed. Rep. of Germany ....... 3201861
Jul. 23, 1982 [DE] Fed. Rep. of Germany ....... 3227554

[51] Int. Cl.⁴ .................... A01N 43/82; C07D 285/12
[52] U.S. Cl. ........................................ 71/90; 544/134; 546/209; 548/138
[58] Field of Search ............................ 548/138; 71/90; 544/134; 546/209

[56] References Cited

U.S. PATENT DOCUMENTS 3,522,267 7/1970 Duerr et al. ................... 548/139
3,784,555 1/1974 Cebalo et al. .................. 71/90
4,269,983 5/1981 Lavanish ....................... 548/139
4,273,574 6/1981 Kirkpatrick ................... 548/140

FOREIGN PATENT DOCUMENTS 47-7549 8/1972 Japan ........................... 548/139

Primary Examiner—Robert Gerstl
Attorney, Agent, or Firm—Keil & Weinkauf

[57] ABSTRACT

Aminothiadiazoles of the formula

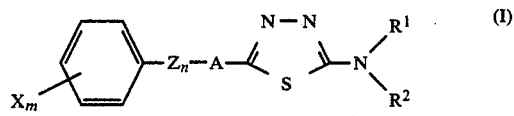

where $R^1$, $R^2$, A, X, Z, m and n have the meanings given in the description, are used for controlling undesirable plant growth.

12 Claims, No Drawings

AMINOTHIADIAZOLES AND THEIR USE FOR CONTROLLING UNDESIRABLE PLANT GROWTH

This application is a continuation of application Ser. No. 457,179, filed on Jan. 11, 1983 now abandoned.

The present invention relates to aminothiadiazoles, herbicides which contain these compounds as active ingredients, and a method of controlling undesirable plant growth with these compounds.

2-Amino-5-phenoxymethyl-1,3,4-thiadiazoles have been disclosed as intermediates for the synthesis of herbicidal 3-(5-phenoxymethyl-1,3,4-thiadiazol-2-yl)imidazolidinones (U.S. Pat. No. 4,252,961). Moreover, it has been disclosed that 2-amino-5-phenyl(alkyl)-1,3,4-thiadiazoles possess pharmacological activity (German Laid-Open Application Nos. DOS 2,212,245, DOS 2,510,439 and DOS 2,126,261). German Laid-Open Application No. DOS 2,336,407 describes herbicidal 2-amino-5-benzyl-1,3,4-thiadiazoles, but these compounds are only effective when applied preemergence.

We have found that aminothiadiazoles of the formula

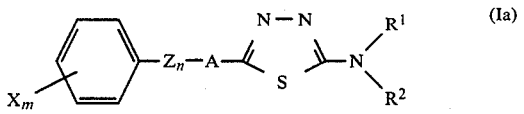

where $R^1$ and $R^2$ independently of one another are each hydrogen, $C_1$–$C_{10}$-alkyl, $C_3$–$C_8$-cycloalkyl, $C_2$–$C_5$-alkoxyalkyl, phenyl, benzyl or 2-phenylethyl, or $R^1$ and $R^2$ together form an alkylene chain of no more than 6 carbon atoms which is unsubstituted or substituted by $C_1$–$C_4$-alkyl and may or may not contain oxygen as a chain member, A is an alkylene chain of 1 to 8 carbon atoms which is unsubstituted or substituted by $C_1$–$C_4$-alkyl, Z is oxygen or sulfur, n is 0 or 1, X is halogen, cyano, nitro, $C_1$–$C_6$-alkyl, $C_1$–$C_6$-alkoxy, $C_1$–$C_4$-haloalkyl, $C_1$–$C_4$-haloalkoxy, $C_1$–$C_4$-alkylthio, $C_1$–$C_4$-alkylsulfonyl, $C_3$–$C_6$-cycloalkyl, phenyl or unsubstituted or halogen-substituted aryloxy, and m is 0, 1, 2, 3 or 4, and where the radical

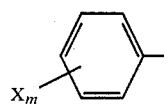

can be replaced by naphthyl which is unsubstituted or substituted by halogen, $C_1$–$C_4$-alkyl or $C_1$–$C_4$-alkoxy, with the proviso that $R^1$ and $R^2$ are not both hydrogen when n is 0 and A is —$CH_2$—, have a herbicidal action and selectively control undesirable plant growth in crop plants.

Novel aminothiadiazoles are those of the formula

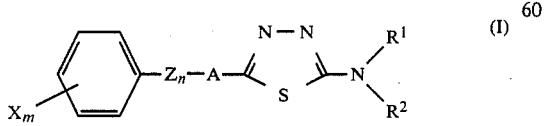

where $R^1$ and $R^2$ independently of one another are each hydrogen, $C_1$–$C_{10}$-alkyl, $C_3$–$C_8$-cycloalkyl, $C_2$–$C_5$-alkoxyalkyl, phenyl, benzyl or 2-phenylethyl, or $R^1$ and $R^2$ together form an aklylene chain of no more than 6 carbon atoms which is unsubstituted or substituted by $C_1$–$C_4$-alkyl and may or may not contain oxygen as a chain member, A is an alkylene chain of 1 to 8 carbon atoms which is unsubstituted or substituted by $C_1$–$C_4$-alkyl, Z is oxygen or sulfur, n is 0 or 1, X is halogen, cyano, nitro, $C_1$–$C_6$-alkyl, $C_1$–$C_6$-alkoxy, $C_1$–$C_4$-haloalkyl, $C_1$–$C_4$-haloalkoxy, $C_1$–$C_4$-alkylthio, $C_1$–$C_4$-alkylsulfonyl, $C_3$–$C_6$-cycloalkyl, phenyl or unsubstituted or halogen-substituted aryloxy and m is 0, 1, 2, 3 or 4, and where the radical

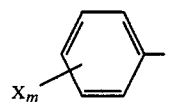

can be replaced by naphthyl which is unsubstituted or substitued by halogen, $C_1$–$C_4$-alkyl or $C_1$–$C_4$-alkoxy, with the proviso that $R^1$ and $R^2$ are not both hydrogen when n is 0, and that $R^2$ is not hydrogen, n-butyl, allyl, cyclohexyl or phenyl when $R^1$ is hydrogen and A is methylene which is unsubstituted or substituted by $C_1$–$C_4$-alkyl.

In formulae I and Ia, $R^1$ and $R^2$ independently of one another may be hydrogen, $C_1$–$C_{10}$-alkyl, preferably $C_1$–$C_4$-alkyl, eg. methyl, ethyl, n-propyl, i-propyl, t-butyl or n-decyl, $C_3$–$C_8$-cycloalkyl, eg. cyclopropyl, cyclohexyl or cyclooctyl, $C_2$–$C_5$-alkoxyalkyl, eg. methoxyethyl or n-propoxyethyl, phenyl, benzyl or 2-phenylethyl, or $R^1$ and $R^2$ together can form an alkylene chain of no more than 6 carbon atoms which is unsubstituted or monosubstituted or polysubstituted by $C_1$–$C_4$-alkyl, preferably by methyl, and may or may not contain oxygen as a chain member, eg. butylene, pentylene, 1,4-dimethylbutylene, 3-oxapentylene or 2,4-dimethyl-3-oxapentylene, A is an unsubstituted or $C_1$–$C_4$-alkyl-substituted alkylene chain or 1 to 8 carbon atoms, eg. methylene, methylmethylene, ethylene, methylethylene, dimethylmethylene, dimethylethylene, porpylene, methylpropylene, ethylmethylene, butylene, pentylene, hexylene, heptylene, methylbutylene or octylene, X is halogen, eg. chlorine, bromine, fluorine or iodine, cyano, nitro, $C_1$–$C_6$-alkyl, $C_1$–$C_6$-alkoxy, $C_1$–$C_4$-alkylthio, $C_1$–$C_4$-haloalkyl, $C_1$–$C_4$-haloalkoxy, $C_1$–$C_4$-alkylsulfonyl, $C_3$–$C_6$-cycloalkyl, phenyl or unsubstituted or halogen-substituted aryloxy, such as unsubstituted or halogen-substituted phenoxy, eg. methyl, ethyl, t-butyl, methoxy, ethoxy, t-butoxy, n-hexyloxy, methylthio, ethylthio, n-butylthio, trifluoromethyl, difluoromethoxy, 1,1,2-trifluoro-2-chloroethoxy, methylsulfonyl, cyclopentyl, cyclohexyl, phenoxy, 4-chlorophenoxy or 2,4-dichlorophenoxy, and Z is oxygen or sulfur.

In formula I, the radical

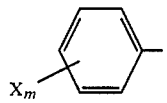

may furthermore be replaced by α- or β-naphthyl which is unsubstituted or substituted by halogen, $C_1$–$C_4$-alkyl or $C_1$–$C_4$-alkoxy, eg. α-naphthyl, β-naphthyl, 4-chloro-α-naphthyl, 7-methoxy-α-naphthyl or 2-methyl-α-naphthyl.

Preferred aminothiadiazoles of the formula Ia are those in which $R^1$ is hydrogen, $R^2$ is $C_1$-$C_4$-alkyl, A is an alkylene chain of 1 to 4 carbon atoms, n is 0 or 1, Z is oxygen, X is halogen or $C_1$-$C_4$-alkyl and m is 1, 2 or 3, and preferred aminothiadiazoles of the formula I are those in which $R^1$ is hydrogen, $R^2$ is $C_1$-$C_4$-alkyl, A is an alkylene chain of 2 to 4 carbon atoms, n is 0 or 1, Z is oxygen, X is halogen or $C_1$-$C_4$-alkyl and m is 1, 2 or 3.

The aminothiazoles of the formula I are obtained by a process wherein a carboxylic acid of the formula

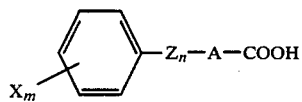 (II)

where A, X, Z, m and n have the above meanings, is reacted with a thiosemicarbazide of the formula

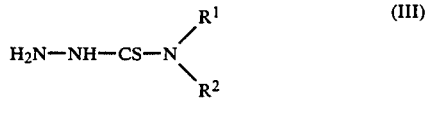 (III)

where $R^1$ and $R^2$ have the above meanings.

This reaction can be carried out in the presence of a solvent which is inert under the reaction conditions, suitable solvents being hydrocarbons, eg. gasoline, toluene and cyclohexane, halohydrocarbons, eg. methylene chloride, chlorobenzene and dichlorobenzene, and ethers, eg. tetrahydrofuran and dioxane. The reaction is carried out at from 0° to 150° C., preferably from 40° to 120° C. It is advantageous to add an agent which eliminates water, eg. sulfuric acid, hydrofluoric acid, polyphosphoric acid, phosphorus pentoxide or phosphorus oxychloride.

EXAMPLE 1

6 g of phosphorus oxychloride were added dropwise, in the course of half an hour, to 25 g of ω-4-chlorophenoxybutyric acid, 10.6 g of thiosemicarbazide and 250 g of dioxane, at 90° C., after which the mixture was stirred under reflux for 1 hour, cooled and then evaporated down in a rotary evaporator. The residue was stirred with water and sufficient sodium hydroxide solution to bring the pH to about 10. The precipitated crystals were filtered off under suction and dried, and the white substance obtained had a melting point of 188°–190° C. and was of the following formula

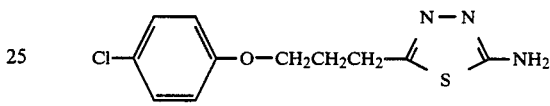

The aminothiadiazoles below, of the formula I or Ia, are prepared by a similar procedure.

| No. | A | $Z_n$ | $X_m$ | $N\begin{smallmatrix}R^1\\R^2\end{smallmatrix}$ | M.p. [°C.] |
|---|---|---|---|---|---|
| 2 | —CH$_2$— | O | 4-Cl | NHCH$_3$ | 138–140 |
| 3 | —CH$_2$— | O | 4-Cl | NH$_2$ | 215–217 |
| 4 | —CH$_2$— | — | 4-phenyl | NHCH$_3$ | 165–167 |
| 5 | —CH$_2$— | — | 4-phenyl | NH$_2$ | 229–231 |
| 6 | —CH$_2$— | — | H | NHCH$_3$ | 117–118 |
| 7 | —CH$_2$— | — | H | NH$_2$ | 178–180 |
| 8 | —(CH$_2$)$_3$— | O | 4-Cl | NHCH$_3$ | 105–107 |
| 9 | —(CH$_2$)$_3$— | O | 4-Cl | NHC$_2$H$_5$ | 98–99 |
| 10 | —(CH$_2$)$_3$— | — | H | NHCH$_3$ | 56–58 |
| 11 | —(CH$_2$)$_3$— | — | H | NH$_2$ | 180–182 |
| 12 | —(CH$_2$)$_4$— | O | 4-Cl | NHCH$_3$ | 83–85 |
| 13 | —(CH$_2$)$_4$— | O | 4-Cl | NH$_2$ | 157–160 |
| 14 | —(CH$_2$)$_2$— | O | 4-C$_4$H$_9$—tert. | NHCH$_3$ | 114–116 |
| 15 | —(CH$_2$)$_3$— | O | 4-C$_4$H$_9$—tert. | NH$_2$ | 194–196 |
| 16 | —(CH$_2$)$_3$— | O | H | NHCH$_3$ | 88–90 |
| 17 | —(CH$_2$)$_3$— | O | 4-C$_2$H$_5$ | NH$_2$ | 178–180 |
| 18 | —(CH$_2$)$_3$— | O | 4-CH$_3$O | NH$_2$ | 186–188 |
| 19 | —(CH$_2$)$_3$— | O | 4-Br | NH$_2$ | 200–202 |
| 20 | —(CH$_2$)$_3$— | O | 3-F | NH$_2$ | 172–174 |
| 21 | —(CH$_2$)$_3$— | O | 2-Cl | NH$_2$ | 184–186 |
| 22 | —(CH$_2$)$_3$— | O | 3,4-Cl$_2$ | NH$_2$ | 164–166 |
| 23 | —(CH$_2$)$_3$— | O | 3,5-Cl$_2$ | NH$_2$ | 171–172 |
| 24 | —(CH$_3$)$_3$— | O | 4-CN | NH$_2$ | 154–156 |
| 25 | —(CH$_2$)$_3$— | O | 3-CH$_3$ | NH$_2$ | 180–182 |
| 26 | —(CH$_2$)$_3$— | O | 4-CH$_3$ | NH$_2$ | 197–200 |
| 27 | —(CH$_2$)$_3$— | O | 3-Cl | NH$_2$ | 149–150 |
| 28 | —(CH$_2$)$_3$— | O | 3-CH$_3$ | NHCH$_3$ | 108–110 |
| 29 | —(CH$_2$)$_3$— | O | 3-Cl | NHCH$_3$ | 85–86 |
| 30 | —(CH$_2$)$_3$— | O | 4-CH$_3$ | NHCH$_3$ | 115–117 |
| 31 | —(CH$_2$)$_3$— | O | 2-Cl | NHCH$_3$ | 68–70 |
| 32 | —(CH$_2$)$_3$— | O | 4-NO$_2$ | NHCH$_3$ | 135–137 |
| 33 | —(CH$_2$)$_3$— | O | 4-CN | NHCH$_3$ | 119–121 |
| 34 | —(CH$_2$)$_3$— | O | 4-Br | NHCH$_3$ | 138–140 |
| 35 | —(CH$_2$)$_3$— | O | 4-OCH$_3$ | NHCH$_3$ | 110–112 |
| 36 | —(CH$_2$)$_3$— | O | 4-t-C$_4$H$_9$ | NHCH$_3$ | 107–109 |
| 37 | —(CH$_2$)$_3$— | O | 4-C$_2$H$_5$ | NHCH$_3$ | 100–102 |
| 38 | —(CH$_2$)$_3$— | O | 3-CF$_3$ | NHCH$_3$ | 78–80 |
| 39 | —(CH$_2$)$_3$— | O | 3,5-Cl$_2$ | NHCH$_3$ | 89–90 |
| 40 | —(CH$_2$)$_3$— | O | 3,4-Cl$_2$ | NHCH$_3$ | 103–105 |
| 41 | —(CH$_2$)$_3$— | O | 2-CH$_3$ | NHCH$_3$ | 84–86 |

-continued

| No. | A | $Z_n$ | $X_m$ | $\begin{array}{c}R^1\\N\\R^2\end{array}$ | M.p. [°C.] |
|---|---|---|---|---|---|
| 42 | —(CH$_2$)$_3$— | O | 3-F | NHCH$_3$ | 72–74 |
| 43 | —(CH$_2$)$_3$— | O | 2,4-Cl$_2$ | NHCH$_3$ | 118–120 |
| 44 | —(CH$_2$)$_3$— | O | 2-CH$_3$, 4-Cl | NHCH$_3$ | 134–138 |
| 45 | —CH(CH$_3$)CH$_2$CH$_2$— | O | 4-Cl | NHCH$_3$ | 109–111 |
| 46 | —CH(CH$_3$)CH$_2$— | — | H | NHCH$_3$ | 83–85 |
| 47 | —CH(CH$_3$)CH$_2$— | — | 4-NO$_2$ | NHCH$_3$ | 132–135 |
| 48 | —CH$_2$— | — | 4-Cl | NHCH$_3$ | 134–136 |
| 49 | —CH$_2$— | — | 2,4-Cl$_2$ | NHCH$_3$ | 128–130 |
| 50 | —CH$_2$— | — | 3-CH$_3$ | NHCH$_3$ | 95–96 |
| 51 | —CH$_2$— | — | 4-OCH$_3$ | NHCH$_3$ | 124–125 |
| 52 | —CH$_2$— | — | 3-CF$_3$ | NHCH$_3$ | 75–76 |
| 53 | —CH$_2$— | — | 3-OCH$_3$ | NHCH$_3$ | 85–87 |
| 54 | —CH$_2$— | — | 2-Cl | NHCH$_3$ | 102–104 |
| 55 | —CH$_2$— | — | 2-OCH$_3$ | NHCH$_3$ | 116–117 |
| 56 | —CH$_2$— | — | 4-CH$_3$ | NHCH$_3$ | 112–114 |
| 57 | —CH$_2$— | — | 2-NO$_2$ | NHCH$_3$ | 68–71 |
| 58 | —CH(C$_2$H$_5$)— | — | H | NHCH$_3$ | 99–100 |
| 59 | —CH$_2$CH$_2$— | — | H | NHCH$_3$ | 102–104 |
| 60 | —C(CH$_3$)$_2$CH$_2$— | — | H | NHCH$_3$ | 147–150 |
| 61 | —C(CH$_3$)$_2$CH$_2$— | — | 4-CH$_3$ | NHCH$_3$ | 132–135 |
| 62 | —CH$_2$—CH(CH$_3$)— | — | 4-t-C$_4$H$_9$ | NHCH$_3$ | 96–97 |
| 63 | —CH$_2$— | O | 2,4-Cl$_2$ | NHCH$_3$ | 141–142 |
| 64 | —CH$_2$— | O | 2-CH$_3$, 4-Cl | NHCH$_3$ | 120–122 |
| 65 | —CH$_2$— | S | 2-CH$_3$, 4-Cl, 5-CH$_3$ | NHCH$_3$ | 155–158 |
| 66 | —CH(CH$_3$)— | O | 2-CH$_3$, 4-Cl | NHCH$_3$ | oil |
| 67 | —CH$_2$—CH$_2$— | O | H | NHCH$_3$ | 98–101 |
| 68 | —CH$_2$—CH$_2$— | O | 4-Cl | NHCH$_3$ | 114–116 |
| 69 | —(CH$_2$)$_3$— | — | 4-OCH$_3$ | NHCH$_3$ | 79–81 |
| 70 | —(CH$_2$)$_4$— | — | H | NHCH$_3$ | 77–79 |
| 71 | —(CH$_2$)$_4$— | — | 4-CH$_3$ | NHCH$_3$ | 103–105 |
| 72 | —(CH$_2$)$_3$— | O | 4-i-C$_3$H$_7$ | NHCH$_3$ | 74–76 |
| 73 | —(CH$_2$)$_4$— | O | H | NHCH$_3$ | 98–100 |
| 74 | —(CH$_2$)$_2$— | — | H | NH$_2$ | 178–180 |
| 75 | —(CH$_2$)$_4$— | O | 2,4-Cl$_2$ | NHCH$_3$ | 74–76 |
| 76 | —(CH$_2$)$_4$— | O | 2-CH$_3$, 4-Cl | NHCH$_3$ | 74–76 |
| 77 | —(CH$_2$)$_4$— | O | 2-CH$_3$ | NHCH$_3$ | 69–71 |
| 78 | —(CH$_2$)$_4$— | O | 3,4-Cl$_2$ | NHCH$_3$ | 80–82 |
| 79 | —(CH$_2$)$_4$— | O | 2-CH$_3$ | NH$_2$ | 143–145 |
| 80 | —(CH$_2$)$_4$— | O | 3,4-Cl$_2$ | NH$_2$ | 135–137 |
| 81 | —(CH$_2$)$_4$— | O | 3-CH$_3$ | NH$_2$ | |
| 82 | —(CH$_2$)$_4$— | O | 3-CH$_3$ | NHCH$_3$ | 70–71 |
| 83 | —(CH$_2$)$_4$— | O | H | NHC$_2$H$_5$ | 94–96 |
| 84 | —(CH$_2$)$_4$— | O | 2-CH$_3$ | NHC$_2$H$_5$ | 57–59 |
| 85 | —(CH$_2$)$_4$— | O | 3,4-Cl$_2$ | NHC$_2$H$_5$ | 96–97 |
| 86 | —(CH$_2$)$_4$— | O | 3-t-C$_4$H$_9$ | NHCH$_3$ | 58–60 |
| 87 | —(CH$_2$)$_5$— | — | 4-CH$_3$ | NHCH$_3$ | 64–66 |
| 88 | —(CH$_2$)$_4$— | — | H | N(CH$_3$)$_2$ | oil |
| 89 | —(CH$_2$)$_3$— | O | 3,4-Cl$_2$ | N(CH$_3$)$_2$ | 98–100 |
| 90 | —(CH$_2$)$_4$— | O | 3,4-Cl$_2$ | N(CH$_3$)$_2$ | oil |
| 91 | —(CH$_2$)$_4$— | — | H | N(C$_2$H$_5$)$_2$ | oil |
| 92 | —(CH$_2$)$_3$— | O | 3,4-Cl$_2$ | N(C$_2$H$_5$)$_2$ | 40–42 |
| 93 | —(CH$_2$)$_4$— | O | 3,4-Cl$_2$ | N(C$_2$H$_5$)$_2$ | oil |
| 94 | —(CH$_2$)$_3$— | O | 3,4-Cl$_2$ | pyrrolidine | 117–119 |
| 95 | —(CH$_2$)$_4$— | O | 3,4-Cl$_2$ | pyrrolidine | oil |
| 96 | —(CH$_2$)$_3$— | O | 3,4-Cl$_2$ | piperidine | 84–85 |
| 97 | —(CH$_2$)$_3$— | O | 3,4-Cl$_2$ | morpholine | 96–97 |
| 98 | —(CH$_2$)$_4$— | — | H | pyrrolidine | 68–70 |
| 99 | —(CH$_2$)$_4$— | — | H | piperidine | 45–47 |
| 100 | —(CH$_2$)$_4$— | — | H | morpholine | 62–64 |
| 134 | —CH$_2$— | — | 3,5-(CH$_3$)$_2$ | NHCH$_3$ | 108–110 |
| 141 | —(CH$_2$)$_4$— | O | 3-Cl | NHCH$_3$ | 75–77 |
| 142 | —(CH$_2$)$_4$— | O | 4-Br | NHCH$_3$ | 101–103 |
| 143 | —(CH$_2$)$_4$— | O | 3-Br | NHCH$_3$ | 79–81 |
| 145 | —(CH$_2$)$_4$— | O | 3,5-(CH$_3$)$_2$ | NHCH$_3$ | 66–67 |
| 147 | —(CH$_2$)$_4$— | O | 3-OCH$_3$ | NHCH$_3$ | oil |
| 148 | —(CH$_2$)$_4$— | O | 3,5-Cl$_2$ | NHCH$_3$ | 65–66 |
| 149 | —(CH$_2$)$_4$— | O | 2,5-Cl$_2$ | NHCH$_3$ | 76–77 |
| 150 | —(CH$_2$)$_4$— | O | 3-NO$_2$ | NHCH$_3$ | 99–101 |
| 151 | —(CH$_2$)$_4$— | O | 2-Cl | NHCH$_3$ | 77–78 |
| 156 | —(CH$_2$)$_6$— | O | 3,4-Cl$_2$ | NHCH$_3$ | 81–83 |
| 157 | —(CH$_2$)$_5$— | O | 3,4-Cl$_2$ | NHCH$_3$ | 84–86 |
| 158 | —(CH$_2$)$_7$— | O | 3,4-Cl$_2$ | NHCH$_3$ | 78–80 |
| 166 | —(CH$_2$)$_3$— | O | 3,4-Cl$_2$ | NH-phenyl | 145–147 |

-continued

| No. | A | $Z_n$ | $X_m$ | $NR^1R^2$ | M.p. [°C.] |
|---|---|---|---|---|---|
| 167 | —(CH$_2$)$_3$— | O | 3,4-Cl$_2$ | NH-benzyl | 125–126 |
| 168 | —(CH$_2$)$_3$— | O | 3,4-Cl$_2$ | NH—CH$_2$CH$_2$—phenyl | 66–67 |
| 189 | —(CH$_2$)$_3$— | O | 3,5-Cl$_2$ | N(i-C$_3$H$_7$)$_2$ | 78–80 |
| 190 | —(CH$_2$)$_3$— | O | 3,4-Cl$_2$ | NH(cycl-C$_6$H$_{11}$) | 85–86 |
| 191 | —(CH$_2$)$_3$— | O | 3,4-Cl$_2$ | N(CH$_3$)phenyl | 85 |
| 192 | —(CH$_2$)$_3$— | O | 3,4-Cl$_2$ | NH(i-C$_3$H$_7$) | 117–118 |
| 193 | —(CH$_2$)$_4$— | O | 3,4-(CH$_3$)$_2$ | NHCH$_3$ | 97–98 |
| 194 | —(CH$_2$)$_4$— | — | 4-Cl | NHCH$_3$ | oil |
| 195 | —(CH$_2$)$_4$— | — | 4-OCH$_3$ | NHCH$_3$ | oil |
| 198 | —(CH$_2$)$_5$— | — | 4-Cl | NHCH$_3$ | 172–175 |

| No. | A | $Z_n$ | $X_m$ | aryl | $NR^1R^2$ | M.p. [°C.] |
|---|---|---|---|---|---|---|
| 184 | —(CH$_2$)$_3$— | O | | α-naphthyl | NHCH$_3$ | 108–110 |
| 185 | —(CH$_2$)$_3$— | O | | β-naphthyl | NHCH$_3$ | 114–116 |
| 186 | —(CH$_2$)$_3$— | O | | β-naphthyl | NH$_2$ | 176–178 |
| 187 | —(CH$_2$)$_4$— | O | | α-naphthyl | NHCH$_3$ | 105–107 |

-continued

| No. | A | $Z_n$ | $X_m$ | aryl | $NR^1R^2$ | M.p. [°C.] |
|---|---|---|---|---|---|---|
| 188 | —(CH$_2$)$_4$— | O | | β-naphthyl | NHCH$_3$ | 123–125 |

The following aminothiadiazoles of the formula I or Ia may be obtained analogously:

| No. | A | $Z_n$ | $X_m$ | $NR^1R^2$ |
|---|---|---|---|---|
| 101 | —(CH$_2$)$_4$— | O | 2,4,5-Cl$_3$ | NHCH$_3$ |
| 102 | —CH$_2$— | O | 4-NO$_2$ | NHCH$_3$ |
| 103 | —C(CH$_3$)$_2$— | O | 2-CH$_3$ | NHCH$_3$ |
| 104 | —(CH$_2$)$_6$— | — | H | NHCH$_3$ |
| 105 | —(CH$_2$)$_6$— | O | H | NHCH$_3$ |
| 106 | —CH$_2$— | S | 4-Cl | NHCH$_3$ |
| 107 | —CH$_2$—CH$_2$CH(CH$_3$)— | O | 4-Cl | NHCH$_3$ |
| 108 | —(CH$_2$)$_3$— | O | 4-F | NHCH$_3$ |
| 109 | —(CH$_2$)$_3$— | O | 2-F | NHCH$_3$ |
| 110 | —(CH$_2$)$_3$— | O | 4-I | NHCH$_3$ |
| 111 | —(CH$_2$)$_3$— | O | 4-Cl | NHC$_3$H$_7$ |
| 112 | —(CH$_2$)$_3$— | O | 4-Cl | NH—i-C$_3$H$_7$ |
| 113 | —(CH$_2$)$_3$— | O | 4-Cl | NHC$_4$H$_9$ |
| 114 | —(CH$_2$)$_3$— | O | 4-Cl | NH—t-C$_4$H$_9$ |
| 115 | —(CH$_2$)$_3$— | O | 4-CF$_3$ | NH—CH$_3$ |
| 116 | —(CH$_2$)$_3$— | O | 4-C$_5$H$_9$ | NH—CH$_3$ |
| 117 | —(CH$_2$)$_3$— | O | 4-C$_6$H$_{13}$ | NH—CH$_3$ |
| 118 | —(CH$_2$)$_3$— | O | 4-(4'-chlorophenoxy) | NH—CH$_3$ |
| 119 | —(CH$_2$)$_3$— | O | 4-(2',4'-dichlorophenoxy) | NH—CH$_3$ |
| 120 | —(CH$_2$)$_3$— | O | 4-phenoxy | NH—CH$_3$ |
| 121 | —(CH$_2$)$_3$— | O | 3-OC$_2$H$_5$ | NH—CH$_3$ |
| 122 | —(CH$_2$)$_3$— | O | 4-OCHF$_2$ | NH—CH$_3$ |
| 123 | —(CH$_2$)$_3$— | O | 3-OCF$_2$CHFCl | NH—CH$_3$ |
| 124 | —(CH$_2$)$_3$— | O | 4-SC$_4$H$_9$ | NH—CH$_3$ |
| 125 | —(CH$_2$)$_3$— | O | H | NH$_2$ |
| 126 | —(CH$_2$)$_2$— | O | 4-Cl | NH$_2$ |
| 127 | —(CH$_2$)$_2$— | O | 4-Cl | NHC$_2$H$_5$ |
| 128 | —(CH$_2$)$_3$— | O | 3-NO$_2$ | NHCH$_3$ |
| 129 | —(CH$_2$)$_3$— | S | H | NHCH$_3$ |
| 130 | —(CH$_2$)$_3$— | S | 4-Cl | NHCH$_3$ |
| 131 | —(CH$_2$)$_3$— | O | 4-SCH$_3$ | NHCH$_3$ |
| 132 | —(CH$_2$)$_3$— | O | 4-SO$_2$CH$_3$ | NHCH$_3$ |
| 133 | —CH$_2$— | — | 2-CH$_3$ | NHCH$_3$ |
| 135 | —CH$_2$— | — | 3,5-Cl$_2$ | NHCH$_3$ |
| 136 | —CH$_2$—CH$_2$— | — | 3,4-Cl$_2$ | NHCH$_3$ |
| 137 | —CH$_2$— | O | 2,4,5-Cl$_2$ | NHCH$_3$ |
| 138 | —CH(CH$_3$)— | O | 2,4-Cl$_2$ | NHCH$_3$ |
| 139 | —(CH$_2$)$_3$— | O | 2,6-(CH$_3$)$_2$ | NHCH$_3$ |
| 140 | —(CH$_2$)$_4$— | O | 4-t-C$_4$H$_9$ | NHCH$_3$ |
| 144 | —(CH$_2$)$_4$— | O | 3-CF$_3$ | NHCH$_3$ |

-continued

| No. | A | $Z_n$ | $X_m$ | $\diagdown N \diagdown {}^{R^1}_{R^2}$ |
|---|---|---|---|---|
| 146 | $-(CH_2)_4-$ | O | 4-OCH$_3$ | NHCH$_3$ |
| 152 | $-(CH_2)_4-$ | O | 2,6-(CH$_3$)$_2$ | NHCH$_2$ |
| 153 | $-(CH_2)_4-$ | O | 3,4-Cl$_2$ | N(i-C$_3$H$_7$)$_2$ |
| 154 | $-(CH_2)_4-$ | O | 3,4-Cl$_2$ | piperidine |
| 155 | $-(CH_2)_4-$ | O | 3,4-Cl$_2$ | morpholine |
| 159 | $-(CH_2)_3-$ | O | 4-Cl | N(CH$_3$)$_2$ |
| 160 | $-(CH_2)_3-$ | O | 4-Cl | N(C$_2$H$_5$)$_2$ |
| 161 | $-(CH_2)_3-$ | O | 4-Cl | pyrrolidine |
| 162 | $-(CH_2)_3-$ | O | 4-Cl | piperdidine |
| 163 | $-(CH_2)_3-$ | O | 4-Cl | morpholine |
| 164 | $-(CH_2)_3-$ | O | 4-Cl | NH-phenyl |
| 165 | $-(CH_2)_3-$ | O | 4-Cl | N(CH$_3$)—phenyl |
| 169 | $-(CH_2)_4-$ | O | 3,4-Cl$_2$ | NH—n-C$_{10}$H$_{22}$ |
| 170 | $-(CH_2)_4-$ | O | 3,4-Cl$_2$ | NH—cycl.C$_6$H$_{11}$ |
| 171 | $-(CH_2)_4-$ | O | 3,4-Cl$_2$ | NH—CH$_2$CH$_2$OCH$_3$ |
| 172 | $-(CH_2)_4-$ | O | 3,4-Cl$_2$ | NH—cycl.C$_3$H$_5$ |
| 173 | $-(CH_2)_4-$ | O | 3,4-Cl$_2$ | (pyrrolidinyl) |
| 174 | $-(CH_2)_4-$ | O | 3,4-Cl$_2$ | (2,6-dimethylmorpholino) |
| 175 | $-(CH_2)_4-$ | S | 4-Cl | NHCH$_3$ |
| 176 | $-(CH_2)_4-$ | — | 4-CH$_3$ | N(CH$_3$)$_2$ |
| 177 | $-(CH_2)_4-$ | — | 4-CH$_3$ | N(C$_2$H$_5$)$_2$ |
| 178 | $-(CH_2)_4-$ | — | 4-CH$_3$ | pyrrolidine |
| 179 | $-(CH_2)_4-$ | — | 4-CH$_3$ | piperidine |
| 180 | $-(CH_2)_4-$ | — | 4-CH$_3$ | morpholine |
| 181 | $-(CH_2)_3-$ | O | 4-O—nC$_6$H$_{13}$ | NHCH$_3$ |
| 182 | $-(CH_2)_3-$ | O | 4-cycl.C$_6$H$_{11}$ | NHCH$_3$ |
| 183 | $-(CH_2)_3-$ | O | 4-Phenyl | NHCH$_3$ |
| 196 | $-(CH_2)_4-$ | — | 3,4-Cl$_2$ | NHCH$_3$ |
| 197 | $-(CH_2)_4-$ | — | 3,5-Cl$_2$ | NHCH$_3$ |

Compounds of formula I and Ia may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 1 is mixed with 10 parts by weight of N-methyl-alpha-pyrrolidone. A mixture is obtained which is suitable for application in the form of very fine drops.

II. 20 parts by weight of compound no. 3 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 5 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 8 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 7 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 6 is intimately mixed with 97 parts by weight of particulate kaolin. A dust is obtained containing 3% by weight of the active ingredient.

VII. 30 parts by weight of compound no. 51 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 1 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or agents may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the objective to be achieved and the growth stage of the plants, and varies from 0.1 to 5 kg/ha and more, but is preferably from 1 to 3 kg/ha.

The herbicidal action of compounds of the formula I and Ia is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the chemicals.

For the postemergence treatment, the plants were first grown in the vessels to a height of from 3 to 15 cm, depending on growth form, before being treated. For this treatment, either plants which had been sown directly in the pots and grown there were selected, or plants which had been grown separately as seedlings and transplanted to the experiment vessels a few days before treatment. No covers were placed on the pots in this treatment method. The application rates for postemergence treatment varied from ingredient to ingredient, and were 1.0, 2.0 and 3.0 kg of active ingredient per hectare.

The pots were set up in the greenhouse—species from warmer areas at from 20° to 35° C., and species from moderate climates at 10° to 20° C. The experiments were run for from 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The test plants employed were Amaranthus spp. *Beta vulgaris, Chenopodium album,* Ipomoea spp., *Galium aparine, Lolium multiflorum, Sinapis alba, Solanum nigrum, Triticum aestivum, Urtica urens,* and *Viola tricolor.*

On postemergence application of 3.0 kg of active ingredient per hectare in the greenhouse, for example compound no. 50 had a good herbicidal action.

On preemergence application of 3.0 kg of active ingredient per hectare, for instance compounds nos. 41, 64, 75, 77 and 101 combated broadleaved plants. Compounds nos. 77 and 78 also combated at lower rates unwanted broadleaved plants selected by way of example, without damaging the crop plants.

In view of the many application methods possible, the compounds according to the invention, or agents containing them, may be used in a large number of crop plants for removing unwanted plant growth.

The following crop plants may be mentioned by way of example:

| Botanical name | Common name |
| --- | --- |
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| Beta vulgaris spp. altissima | sugarbeets |
| Beta vulgaris spp. rapa | fodder beets |
| *Brassica napus* var. *napobrassica* | |
| *Brassica napus* var. *rapa* | turnips |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora, Coffea liberica*) | coffee plants |
| *Cynodon dactylon* | Bermudagrass in turf and lawns |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum Gossypium herbaceum Gossypium vitifolium*) | cotton |
| *Helianthus annuus* | sunflowers |
| *Helianthus tuberosus* | |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicothiana tabacum* (*N. rustica*) | tobacco |
| *Olea europaea* | olive trees |
| *Oryza sativa* | rice |
| *Panicum miliaceum* | |
| *Phaseolus lunatus* | limabeans |
| *Phaseolus mungo* | mungbeans |
| *Phaseolus vulgaris* | snapbeans, green beans, dry beans |
| *Pennisetum glaucum* | |
| *Petroselinum crispum* | parsley |

| Botanical name | Common name |
| --- | --- |
| spp. tuberosum | |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Sesamum indicum* | sesame |
| *Solanum tuberosum* | Irish potatoes |
| *Sorghum bicolor* (*s. vulgare*) | sorghum |
| *Sorghum dochna* | |
| *Spinacia oleracea* | spinach |
| *Theobroma cacao* | cacao plants |
| *Trifolium pratense* | red clover |
| *Triticum aestivum* | wheat |
| *Vaccinium corymbosum* | blueberries |
| *Vaccinium vitis-idaea* | cranberries |
| *Vicia faba* | tick beans |
| *Vigna sinensis* (*V. unguiculata*) | cow peas |
| *Vitis vinifera* | grapes |
| *Zea mays* | Indian corn, sweet corn, maize |

To increase the spectrum of action and to achieve synergistic effects, the compounds according to the invention, or herbicidal agents containing them, may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc.

It may also be useful to apply the compounds of the formula I and Ia, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Nonphytotoxic oils and oil concentrates may also be added.

We claim:

1. An aminothiadiazole of the formula

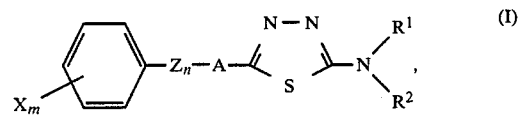

where $R^1$ and $R^2$ independently of one another are each hydrogen, $C_1$–$C_{10}$-alkyl, $C_3$–$C_8$-cycloalkyl, $C_2$–$C_5$-alkoxyalkyl, phenyl, benzyl, 2-phenylethyl, or $R^1$ and $R^2$ together form a butylene, pentylene, 1,4-dimethyl-3-oxapentylene or 2,4-dimethyl-3-oxapentylene group, A is an alkylene chain of 2 to 4 carbon atoms which is unsubstituted or substituted by $C_1$–$C_4$-alkyl, Z is oxygen, n is 0 or 1, X is halogen, cyano, nitro, $C_1$–$C_6$-alkyl, $C_1$–$C_6$-alkoxy, $C_1$–$C_4$-haloalkyl, $C_1$–$C_4$-alkylthio, $C_1$–$C_4$-alkylsulfonyl, $C_3$–$C_6$-cycloalkyl, phenyl or unsubstituted or halogen-substituted aryloxy and m is 0, 1, 2, 3 or 4, and where the radical

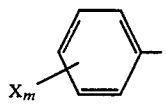

can be replaced by naphthyl which is unsubstituted or substituted by halogen, $C_1$-$C_4$-alkyl or $C_1$-$C_4$-alkoxy, with the proviso that $R^1$ and $R^2$ are not both hydrogen.

2. An aminothiadiazole of the formula I as defined in claim 1, where $R^1$ is hydrogen, $R^2$ is $C_1$-$C_4$-alkyl, A is an alkylene chain of 2 to 4 carbon atoms, n is 0 or 1, Z is oxygen, X is halogen or $C_1$-$C_4$-alkyl, and m is 1, 2 or 3.

3. 2-[4-(2-Methyl-phenoxy)-n-butanyl]-5-methylamino-1,3,4-thiadiazole.

4. An aminothiadiazole of the formula I as defined in claim 1, wherein n is 1.

5. A compound of the formula I as defined in claim 1, which is (5-[5-(4-methyl-phenoxy-n-pentyl]-2-methylamino-1,3,4-thiadiazole.

6. An aminothiadiazole of the formula

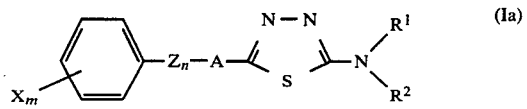

where $R^1$ and $R^2$ independently of one another are each hydrogen, $C_1$-$C_{10}$-alkyl, $C_3$-$C_8$-cycloalkyl, $C_2$-$C_5$-alkoxyalkyl, phenyl, benzyl, 2-phenylethyl, or $R^1$ and $R^2$ together form a butylene, pentylene, 1,4-dimethyl-3-oxapentylene or 2,4-dimethyl-3-oxapentylene group, A is ethylene, methylethylene, dimethylethylene, propylene, methylpropylene, butylene, or methylbutylene, Z is oxygen, n is 0 or 1, X is halogen, cyano, nitro, $C_1$-$C_6$-alkyl, $C_1$-$C_6$-alkoxy, $C_1$-$C_4$-haloalkyl, $C_1$-$C_4$-alkylthio, $C_1$-$C_4$-alkylsulfonyl, $C_3$-$C_6$-cycloalkyl, phenyl or unsubstituted or halogen-substituted aryloxy and m is 0, 1, 2, 3 or 4, with the proviso that $R^1$ and $R^2$ are not both hydrogen.

7. A herbicide containing inert additives and an aminothiadiazole of the formula I as defined in claim 1.

8. A herbicide as defined in claim 7, where the aminothiadiazole of the formula I is one in which $R^1$ is hydrogen, $R^2$ is $C_1$-$C_4$-alkyl, A is an alkylene chain of 2 to 4 carbon atoms, n is 0 or 1, Z is oxygen, X is halogen or $C_1$-$C_4$-alkyl, and m is 1, 2 or 3.

9. A herbicide containing an inert carrier and/or diluent and from 0.1 to 95% by weight of an aminothiadiazole of the formula where $R^1$ and $R^2$ independently of one another are each hydrogen, $C_1$-$C_{10}$-alkyl, $C_3$-$C_8$-cycloalkyl, $C_2$-$C_5$-alkoxyalkyl, phenyl, benzyl, 2-phenylethyl, or $R^1$ and $R^2$ together form a butylene, pentylene, 1,4-dimethyl-3-oxapentylene or 2,4-dimethyl-3-oxapentylene group, A is an alkylene chain of 1 to 8 carbon atoms which is unsubstituted or substituted by $C_1$-$C_4$-alkyl, Z is oxygen or sulfur, n is 0 or 1, X is halogen, cyano, nitro, $C_1$-$C_6$-alkyl, $C_1$-$C_6$-alkoxy, $C_1$-$C_4$-haloalkyl, $C_1$-$C_4$-haloalkoxy, $C_1$-$C_4$-alkylthio, $C_1$-$C_4$-alkylsulfonyl, $C_3$-$C_6$-cycloalkyl, phenyl or unsubstituted or halogen-substituted aryloxy and m is 0, 1, 2, 3 or 4, and where the radical can be replaced by naphthyl which is unsubstituted or substituted by halogen, $C_1$-$C_4$-alkyl or $C_1$-$C_4$-alkoxy, with the proviso that $R^1$ and $R^2$ are not both hydrogen when n is 0 and A is —$CH_2$—.

10. A herbicide as defined in claim 9, where the aminothiadiazole of the formula Ia is one in which $R^1$ is hydrogen, $R^2$ is $C_1$-$C_4$-alkyl, A is an alkylene chain of 1 to 4 carbon atoms, n is 0 or 1, Z is oxygen, X is halogen or $C_1$-$C_4$-alkyl, and m is 1, 2 or 3.

11. A process for combating unwanted plant growth, wherein a herbicidally effective amount of an aminothiadiazole of the formula I as defined in claim 1 is allowed to act on the plants and/or their location.

12. A process for combating unwanted plant growth, wherein a herbicidally effective amount of an aminothiadiazole of the formula Ia as defined in claim 9 is allowed to act on the plants and/or their location.

* * * * *